United States Patent [19]

Chou et al.

[11] Patent Number: 5,281,746
[45] Date of Patent: Jan. 25, 1994

[54] PROCESS FOR PREPARING PEROXYACID PRECURSORS HAVING AMIDE MOIETIES IN THE FATTY CHAIN

[75] Inventors: Yueting Chou, Chesterfield; Martin A. Kreczmer, St. Peters; David A. Martin, Ballwin, all of Mo.

[73] Assignee: Monsanto Company, St. Louis, Mo.

[21] Appl. No.: 11,579

[22] Filed: Feb. 1, 1993

[51] Int. Cl.5 .......................................... C07C 229/00
[52] U.S. Cl. ..................................................... 560/155
[58] Field of Search ......................................... 560/155

[56] References Cited

U.S. PATENT DOCUMENTS

| | | | |
|---|---|---|---|
| 2,604,449 | 7/1952 | Bryant | 560/155 |
| 2,627,487 | 2/1953 | Drake | 560/155 |
| 2,742,432 | 4/1956 | Messina | 560/155 |
| 3,214,460 | 10/1965 | McGee | 560/155 |
| 3,417,114 | 12/1968 | Kuceski | 560/155 |
| 3,816,510 | 6/1974 | Massie | 560/155 |
| 4,588,833 | 5/1986 | Kadelka | 560/155 |
| 4,852,989 | 8/1989 | Burns | 560/155 |
| 5,166,407 | 11/1992 | Alul | 560/155 |
| 5,231,215 | 7/1993 | Engladnder | 560/155 |
| 5,235,093 | 8/1993 | Cova | 560/155 |

FOREIGN PATENT DOCUMENTS 0445096 9/1991 European Pat. Off. .

*Primary Examiner*—Michael L. Shippen
*Attorney, Agent, or Firm*—R. Loyer

[57] ABSTRACT

A process for preparing precursors for amide containing organic peracids is disclosed wherein a polycarboxylic acid is esterified with a low molecular weight alkyl alcohol followed by formation of an amide by reacting the ester with an amine to provide a monoamido carboxylic acid ester. Unwanted diester is removed from the reaction mixture by precipitation at relatively low temperature. The ester is recovered from the reaction mixture by either precipitation or a distillation procedure under high temperature and reduced pressure. The esters are converted to acids highly desirable as precursors for peracids useful as bleaches in laundry detergents.

12 Claims, No Drawings

PROCESS FOR PREPARING PEROXYACID PRECURSORS HAVING AMIDE MOIETIES IN THE FATTY CHAIN

This invention relates to the preparation of fatty acids which are to be oxidized to provide bleaching compounds comprised of fatty peroxyacids and salts thereof.

BACKGROUND OF THE INVENTION

The discovery of highly stable organic peracid molecules is critical to the commercialization of detergent formulations containing peracid bleaches. Such bleaches have recently been discovered which are highly crystalline in nature and have relatively high melting points. Also, it is very important for highly stable bleaches to be prepared in a manner which eliminates, or at least minimizes their contamination from metals. Metals or metal ions are particularly deleterious to peracids as they catalyze the decomposition of the peroxygen group.

Consequently, the detergent industry requires peracids which are highly stable, have high melting points and are conveniently manufactured in large volumes. Because of their high melting points both the peracids and their precursors are typically purified by precipitation or crystallization techniques. Metal ions typically present in the crystallization media become trapped in the peracid crystals and become impurities which reduce the stability of the peracid. The amount of metal ion contamination is directly related to stability of the peracid.

A recent patent, U.S. Pat. No. 4,634,551 to Burns et al describes novel, relatively stable and high melting crystalline amide peracids. Generally, the precursors to these amide peracids, that is, the amido acids, are reported to have been prepared by the reaction of the appropriate acid chloride with the appropriate amine followed by precipitation of the resulting amido acid. Stability of these amide peracids is affected not only by metal contamination but also by the chloride impurity. Attempts to purify the peracid have proven inadequate to economically remove metals and chlorides. Even purification of the amine precursor is not adequate to provide an economical product of sufficient purity for use in preparing the peracid.

The peroxyacids found in U.S. Pat. No. 4,634,551 are represented by the formula

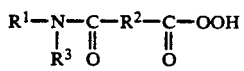

where in $R^1$ is selected from the groups consisting of alkyl, aryl or alkaryl radicals containing from about 1 to about 14 carbon atoms, $R^2$ is an alkylene group containing from 2 to 14 carbon atoms and $R^3$ is H or an alkyl, aryl or alkaryl group containing from 1 to about 10 carbon atoms, the total number of carbon atoms being from about 10 to about 20.

There has been a need for an efficient, high volume means of producing the above described amide acid in high purity and with good stability. It has been discovered that one means of efficiently providing the amide acid precurser in high volumes is by a process which first prepares a monoamido ester of a dicarboxylic acid and then converts the ester to a peracid. The monoamido ester is prepared by esterifying a polycarboxylic acid of the formula

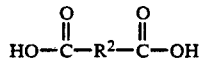

with a lower alkyl alcohol and then reacting the ester with a mono alkyl amine of the formula

wherein R is an alkyl radical having from 1 to 20 carbon atoms and $R^2$ is as defined above. A mixture of monoamide and diamide is thus produced.

The reaction mixture obtained by the reaction of the ester and the amine is distilled under reduced pressure to selectively remove the monoamide carboxylic acid ester from the reaction mixture. Such a process is described in EP 0 445 096 which is incorporated herein by reference. It has been found that such distillation efficiently separates the desired product of this invention but, the stress of the high temperatures and reduced pressures which are necessary causes color forming bodies of undefined nature to be created. These color forming bodies and a small amount of the diamide codistill with the distilled product in spite of a strenuous three stage distillation process.

Accordingly, there is needed a process for efficiently preparing the fatty peroxyacids or salts thereof having an amide moiety in very high volume and purity particularly with the absence of color forming bodies. In particular, there is needed for a process which permits lower distillation temperatures, thus reducing the thermal stress on the desired product while providing high product purity without the loss of product in the still bottoms.

BRIEF DESCRIPTION OF THE INVENTION

In accordance with this invention a process is provided for efficient preparation of precursors of fatty peroxyacids or salts thereof, having amide moieties in the fatty chain. One aspect of this invention is a process which provides the above mentioned peroxyacid precursors in a manner which greatly reduces the amount of diamide going to the final distillation step and consequent entrainment of such undesired contaminant into the final product of the above mentioned peroxyacid. In another aspect of this invention, said precursors are prepared by a process employing lower distillation temperatures, while yet maintaining an efficient distillation thereby avoiding contamination of the product by color forming bodies.

More specifically, this invention provides a process for preparing a monoamido ester of a dicarboxylic acid by first esterifying a polycarboxylic acid of the formula

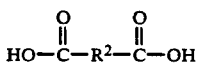

with a lower alkyl alcohol and then by reacting the diester with a monoalkylamine of the formula

wherein R is an alkyl radical having from 1 to 20 carbon atoms and $R^2$ is as defined above.

The reaction mixture obtained by the reaction of the diester and the amine contains a major amount of the desired amide ester, a large amount of unreacted diester and a considerable amount of unwanted but unavoidable diamide. In accordance with this invention, the reaction mixture is then cooled to a temperature in the range of about 35° C. whereby virtually all of the unwanted diamide precipitates. Removal of the precipitate by such ordinary means as filtration produces a mother liquor which can be efficiently distilled under reduced pressure, but at lower temperatures than heretofore possible, to remove the monoamide carboxylic acid ester from the unreacted diester. The operation in accordance with this invention is not as critical as when performed in the presence of the diamide. It has been found that such distillation efficiently separates the desired product from the remainder of the reaction mixture. The process of this invention can provide amido esters and, when such esters are hydrolyzed by conventional means, amido acids which can be converted to peracids.

DETAILED DESCRIPTION OF THE INVENTION

Typical dibasic acids include those having from 2 to 14 carbon atoms between the carboxyl groups. Preferably the dibasic acids useful in this invention contain from about 6 to about 12 carbon atoms between the carboxyl groups and are aliphatic, straight chained. Included are adipic acid, glutaric acid, succinic acid, pimelic acid, suberic acid, azelaic acid, sebacic acid, and dodecanedioic acid.

Any number of alcohols may be employed to provide the diester. However, since the final product is a monoamide which is separated from a reaction mixture containing large amounts of unreacted diester, the alcohol is chosen so as to provide easily distinguishable properties between the diester and monamide. Accordingly, any suitable ester forming alcohol may be employed in the first step of the process of this invention. Examples of such alcohols are methanol, ethanol, propanol, isopropanol, n-butanol, hexanol, octanol, and other low molecular weight alkyl alcohols. Alkyl alcohols containing from about 1 to 4 carbon atoms are preferred and normal alcohols are preferred when higher molecular weight alcohols are employed. Methanol is preferred when the dibasic acid is adipic acid. Esterification is described in EPO 445096 referred to above.

In the next step of the process of this invention, the diester is reacted with an amine to provide a distillable monoamide ester. The alcohol formed is removed and recycled. The reaction is monitored by GC analysis or by titration of the reaction mixture for residual amine. It is usual that the reaction providing the amide takes place almost instantaneously at higher temperatures and in about 1 to about 5 hours at a temperature in the range of from about 70° C. to about 150° C. The reaction between the amine and the ester is carried out with an excess of ester to maximize production of the desired monoamido ester and to minimize formation of diamide by-product. Such excess is surprisingly large to provide the monoamide. Excess as high as 20 to 1 on a mole basis may be employed. In most instances the excess of diester over amine is in the range of from about 3 to 10 moles of diester per mole of amine. The mole ratio is preferably about 8 to 10 moles of diester to 1 mole of amine.

Amines employed in the process of this inventions are primary amines containing either straight or branched chain alkyl groups. Typically the amine contains from 1 to 20 carbon atoms and preferably from about 6 to about 12 carbon atoms. Such preferred amines are commercially available. Typical amines include hexylamine, heptylamine, octylamine, nonylamine, decylamine, dodecyclamine and undecyl amine. The linear or straight chain alkyl amines are preferred because the final amido acids have higher melting points than those of branched chained amido acids.

To provide a high purity monoamide ester product the reaction mixture is cooled to a temperature below about 40° C. and usually in the range of from about 30° C. to about 35° C. The diamide precipitates in the form of easily filterable crystals which are then removed from the reaction mixture by typical liquid-solid separation devices. Such conventional methods employ the use of belt or drum filters and centrifuges. The remaining liquor is then subjected to distillation to recover the monoamido ester as an overhead product, without any substantial amount of diamide present. The distillation proceeds efficiently at pot temperatures in the range of from about 200° C. to about 225° C. at a pressure in the range of from about 0.5 mm Hg (133.32 $N/m_2$) to about 1.5 mm Hg (399.96 $N/m^2$).

Alternately, the mother liquor from the initial filtration step may be subjected to a second precipitation and filtration or centrifugation step to recover the desired monoamido ester. The second precipitation and filtration step takes place at even lower temperatures than employed in the removal of the diamide. In this embodiment, the mother liquor from the diamide removal step is further cooled to below about 18° C. and most usually in the range of from about 10° C. to about 15° C. The desired monoamido ester precipitates and is easily separated by filtration or centrifugation as noted above in the case of the diamide.

In either of the two above embodiments wherein the precipitate is recovered, the recovered crystals are advantageously washed and the wash liquor combined with the filtrate to recover the maximum amount of material. In the preferred embodiment of this invention, recycled diester is employed to wash the precipitate. In the case of the diamide, additional mono amido ester is recovered by washing the diamide crystals with cooled diester and the wash liquor combined with the filtrate. Likewise, the precipitated monoamido ester can be washed with cooled diester to purify the desired product. After washing with cooled diester the monoamido ester crystals may be washed with water to further purify the crystals. Thus, from the above, it can be seen that in accordance with this invention, the desired monoamido ester is advantageously recovered from the reaction mixture in different ways after removal of the diamide. The desired monoamide ester is recovered by either precipitation under cold conditions or by distillation whereby the diester is first distilled from the mixture followed by the monoamido ester. There is thus provided a more easily separated mixture by early removal of the diester.

In the embodiment whereby the monoamido ester is removed by distillation, such operation is normally conducted in a two-step distillation procedure. The unreacted diester and traces of amine are first removed by distillation at relatively low temperature. Thereafter, the desired monoamide is recovered by either distillation at higher temperature under reduced pressure or preferably by crystallization. The term "reduced pressure" in this specification and claims means pressure within the distillation column of no more than about 10 mm Hg (1;333.224 N/m²). Such reduced pressure is maintained during recovery of the desired monoamide ester. The temperature of the distillation depends upon the dibasic acid and the amido group. Usually, the temperature employed to distill the monoamide is in the range of from about 100° C. to about 300° C. but this depends upon the specific material being recovered.

DESCRIPTION OF THE PREFERRED EMBODIMENTS

EXAMPLE 1

A crude reaction mixture from the reaction of nonylamine with dimethyl adipate is refined by heating 505.9 g of the mixture to about 70° C. to keep the desired materials in solution. The heated mixture was then filtered hot (above 60° C.) to remove a small amount of undissolved material. The wet cake weighed 5.3 g leaving 496.2 ml of filtrate. A step loss of 3 g occurred. The filtrate was then cooled to 35° C. forming solids which were filtered off at a temperature in the range of from about 30° C. to about 35° C. The wet cake comprising dinonylamidoadipate from this step weighed 27.2 g leaving 511.2 ml of filtrate after a wash of the filter cake with a small amount (27.2 g) of dimethyl adipate. A step loss of 4.5 g occurred. The filtrate from the removal of dimethyl adipate (509.2 g) was then cooled to a temperature in the range of 13° C.-14° C. whereupon nonyl amido solids formed. The solids were white crystals comprising nonylamido methyl adipate which were filtered off while cold (13° C.-15° C.). The wet cake consisted of nonylamido methyl adipate and weighed 75.3 g leaving 428.3 ml of filtrate. The filtrate was transferred to a distillation flask and the unreacted dimethyl ester of adipic acid is recovered overhead by heating the contents of the flask to about 72° C. at a reduced pressure of 0.4 mm Hg (53.33 N/m²). A distillate of 353.5 ml was obtained leaving 70.7 ml in the distillation flask. The recovered dimethyl ester of adipic acid could be employed as wash liquor for the several crops of crystalline product obtained in the above described process.

EXAMPLE 2

A portion (1750 g) of a reaction product from the reaction of nonylamine with dimethyl adipate diester at a molar ratio of 1:8, respectively, was first heated to dissolve the contents and then cooled to 35° C. and filtered. A wet cake weighing 28.8 g comprising dinonyl amidoadipate was obtained which was washed with 40.8 g of recycled dimethyl adipate diester. A total of 1,716 ml of filtrate was then fed to a two-step distillation system. A forecut of dimethyl adipate diester (1,395.4 g) was obtained at a temperature below 200° C., and 1.3 mm Hg (173.32 N/m₂). The main cut (265.6 g) of nonylamido methyl adipate was collected over a period of 1 hour 15 min. at 217° C. and a pressure of 1.6 mm Hg (213.31 N/m²). A residue of 4.8 g was left in the still.

There has been described above the preparation of amido esters of dibasic acids represented by the formula:

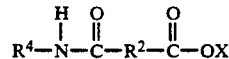

wherein $R^4$ is an alkyl group having from 1 to 20 carbon atoms, $R^2$ is an alkylene group containing from 2 to 14 carbon atoms and X is an alkyl radical having from 1 to 8 carbon atoms. These amido esters may be hydrolyzed in the usual way to provide amido acids represented by the formula:

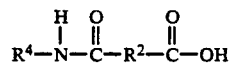

wherein $R^2$ and $R^4$ are as defined above. These and acids have been found to be excellent precursor compounds of amido peracids.

What is claimed is:

1. A process for the preparation of a monoamido ester of a dibasic acid represented by the formula

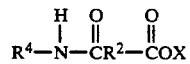

wherein $R^4$ is an alkyl group having from 1 to 20 carbon atoms, $R^2$ is an alkylene group containing from 2 to 14 carbon atoms and X is an alkyl radical having from 1 to 8 carbon atoms which comprises the steps of:
(a) esterifying a polycarboxylic acid of the formula

by reaction with an alkyl alcohol having from 1 to 8 carbon atoms;
(b) reacting the diomide of the diacid of (a) with monoalkyl amine of the formula

wherein R is an alkyl radical having from 1 to 20 carbon atoms wherein there is provided a molar excess of diester of up to about 20 to 1;
(c) cooling the reaction mixture of (b) to a temperature below about 35° C. whereby the diomide of said polycarboxylic acid formed in the reaction of (b) precipitates and separating said precipitate from the reaction mixture; and
(d) removing the mono amido ester formed in step (b) from the reaction mixture.

2. The process of claim 1 wherein the mono amino ester is removed by cooling the reaction mixture obtained from step (c) to a temperature in the range of from about 10° C. to about 20° C. whereby said ester precipitates.

3. The process of claim 1 wherein the mono amido ester is removed by distilling the reaction mixture obtained from step (c) under reduced pressure.

4. The process of claim 1 wherein the amine is n-nonylamine.

5. The process of claim 4 wherein the mono amido ester is distilled at a temperature in the range of from about 220° C. to about 225° C.

6. The process of claim 5 wherein the alcohol is methanol.

7. The process of claim 6 wherein the polycarboxylic acid is adipic acid.

8. The process of claim 4 wherein the distillation of the monoamide is carried out under reduced pressure in the range of up to about 1 mm Hg.

9. The process of claim 3 wherein the distillation is performed in at least two steps and in the first step the unreacted diester and amine are removed and in the second step the monoamide is removed.

10. The process of claim 6 wherein methanol is also the solvent for the acid.

11. The process of claim 1 wherein the dibasic acid is selected form the group consisting of succinic, glutaric, adipic, suberic and azealic acids.

12. The process of claim 1 wherein the amine contains from 6 to 12 carbon atoms.

* * * * *